United States Patent
Miar et al.

(10) Patent No.: US 12,029,815 B2
(45) Date of Patent: Jul. 9, 2024

(54) MUCOADHESIVE PATCH AND USES THEREOF

(71) Applicant: Board of Regents, The University of Texas System, Austin, TX (US)

(72) Inventors: Solaleh Miar, San Antonio, TX (US); Gregory Robert Dion, Schertz, TX (US); Joo Leng Ong, San Antonio, TX (US); Teja Guda, San Antonio, TX (US)

(*) Notice: Subject to any disclaimer, the term of this patent is extended or adjusted under 35 U.S.C. 154(b) by 239 days.

(21) Appl. No.: 17/321,370

(22) Filed: May 14, 2021

(65) Prior Publication Data
US 2021/0353529 A1 Nov. 18, 2021

Related U.S. Application Data

(60) Provisional application No. 63/024,910, filed on May 14, 2020.

(51) Int. Cl.
| | |
|---|---|
| A61K 9/00 | (2006.01) |
| A61F 13/00 | (2024.01) |
| A61F 13/01 | (2024.01) |
| A61K 31/573 | (2006.01) |
| D01D 5/00 | (2006.01) |
| D06M 15/27 | (2006.01) |

(52) U.S. Cl.
CPC ........ *A61K 9/006* (2013.01); *A61F 13/00063* (2013.01); *A61F 13/01017* (2024.01); *A61F 13/01021* (2024.01); *A61K 31/573* (2013.01); *D01D 5/003* (2013.01); *D06M 15/27* (2013.01); *A61F 2013/00089* (2013.01); *D10B 2331/041* (2013.01)

(58) Field of Classification Search
CPC . A61K 9/006; A61K 31/573; A61F 13/00017; A61F 13/00021; A61F 13/00063
See application file for complete search history.

(56) References Cited

U.S. PATENT DOCUMENTS

| | | | | |
|---|---|---|---|---|
| 2007/0014773 | A1* | 1/2007 | Matheny | A61K 35/22 435/366 |
| 2011/0293685 | A1* | 12/2011 | Kuo | A61L 31/146 424/422 |
| 2014/0148846 | A1* | 5/2014 | Pereira | A61L 15/26 424/443 |

OTHER PUBLICATIONS

Walther et al., "Development of Novel Scaffolds for tissue Engineering by Flock Technology", Textile Research Journal, vol. 77 (11)-892-899, 2007. (Year: 2007).*

* cited by examiner

*Primary Examiner* — Jianfeng Song
(74) *Attorney, Agent, or Firm* — Nevrivy Patent Law Group P.L.L.C.

(57) ABSTRACT

The present invention provides a mucoadhesive patch for attachment to a mucosal surface in a patient, the patch comprising a fibrous polymeric mat substrate and a plurality of polymeric flock particles that are attached to the substrate.

10 Claims, 7 Drawing Sheets

MUCOADHESIVE PATCH AND USES THEREOF

CROSS-REFERENCE TO RELATED APPLICATIONS

This application claims the benefit of U.S. Provisional Appl. No. 63/024,910, filed May 14, 2020, which is incorporated by reference herein.

FIELD OF THE INVENTION

The field of the invention relates to medicine, devices, and biomaterials, in particular to devices and materials useful for treating diseases or conditions, such as esophageal or laryngotracheal diseases or conditions.

BACKGROUND OF THE INVENTION

Esophageal and laryngotracheal wound closure is complicated by unique three-dimensional anatomy, exposure to commensal, presence of mucus and secretions, and the overarching need for achieving an air- and water-tight closure. Furthermore, the healing trachea and esophagus must remain functional in the absence of a tracheostomy or percutaneous endoscopic gastrostomy tube. Penetrating wounds to the larynx, trachea and esophagus most often occur during surgical intervention or from trauma. Recent evaluation identified acute laryngeal injury in more than half of patients intubated >12 hours, with findings persisting for >2 months (Shinn et al., Critical care medicine, (2019), 47:1699-1706). Although less common, esophageal injuries from caustic ingestion are a significant health burden in the pediatric population, and esophageal perforations demonstrate significant morbidity (Sdralis et al., Dis Esophagus, (2017), 30:1-6; Hoffman et al., N Engl J Med, (2020), 382:1739-1748). Inadequate wound closure results in serious complications including pneumomediastinum, deep neck space infection, or mediastinitis (DeMers et al., The American Journal of Emergency Medicine, (2011), 29:841.e843-841.e848; Velhonoja et al., European Archives of Oto-Rhino-Laryngology, (2020), 277:863-872; Yu et al., Interactive CardioVascular and Thoracic Surgery, (2013), 17:861-866). Currently, the most widely employed closure techniques are primary closure and overlay with adjacent muscle tissue (Huu et al., Asian cardiovascular & thoracic annals, (2019), 27:192-198). Evidence suggests that early intervention may be ideal for treating patients, since few effective alternatives exist (Nouraei et al., Laryngoscope, (2006), 116:1417-1421).

Adjuvant closure techniques for esophageal and laryngotracheal wounds include salivary bypass tubes, stents, and skin grafting (Nouraei et al., Laryngoscope, (2013), 123: 2474-2484; Bowe et al., Int J Pediatr Otorhinolaryngol, (2018), 108:46-48; Kim et al., Ann Thorac Surg, (2008), 85:1962-1967, discussion 1967; Chen et al., JAMA Otolaryngol Head Neck Surg 2020; Moonsamy et al., Ann Cardiothorac Surg, (2018), 7:210-216. These have had mixed success and are limited by associated morbidity from salivary bypass tubes or secondary harvest sites and subsequent skin graft changes which may still not provide air- or water-tight closure (Nouraei et al., Laryngoscope, (2013), 123:2474-2484; Kim et al., Ann Thorac Surg, (2008), 85:1962-1967, discussion 1967). Additionally, few available stents are capable of delivering therapeutics. Application of biomaterial and tissue-engineered products holds promise as evidenced by preliminary data using connective tissue-based biosheets for esophagoplasty (Okuyama et al., Journal of pediatric surgery, (2018), 53:223-226).

Recent advances in biomimetic materials provide unique opportunities for new technology targeting unmet clinical needs. Specifically, recent work leveraging the mechanism geckos and mussels use to attach to wet, irregular surfaces; holds promise in inspiring materials designed for adhesion in moist environments (Lee et al., Nature, (2007), 448:338-341; Menguc et al., J R Soc Interface, (2014), 11:20131205). These new materials are manufactured by adapting flocking technology from the textile industry whereby short, vertical fibers are affixed to a base layer to design the composite construct (Walther et al., Textile Research Journal, (2007), 77:892-899). These composites can potentially provide improved, reversible adhesion compared to traditional biopolymers (Kim et al., Applied Physics Letters, (2007), 91:221913; Tamelier et al., *SENSORS, 2011 IEEE*, 2011: 1819-1822). Originally envisioned as adhesive tapes or as stability mechanisms in robotic climbers, they can also function as scaffolds in tissue engineering (Vellayappan et al., RSC Advances 2015; 5:73225-73240).

The design of a base layer for tissue sealants requires materials capable of conforming to the gross anatomy that control fluid permeability, while maintaining biocompatibility. Electrospinning is the preferred technique for creating fibrous mats in controlled, designed architectures. Electrospun fibers are manufactured by applying high voltage between a nozzle and collector to create a polymer stream, and can be optimized for desired fiber diameter, orientation and mat thickness (Cipitria et al., Journal of Materials Chemistry 2011; 21:9419-9453). A variety of polymers can be electrospun for biomedical applications (Cipitria et al., Journal of Materials Chemistry 2011; 21:9419-9453; Varagnolo et al., RSC Adv, (2017), 7:5836-5842; Coimbra et al., Mater Sci Eng C Mater Biol Appl, (2019), 94:86-93). Polycaprolactone (PCL), a biocompatible polymer is of specific interest for tissue engineering since it presents low inflammatory response, especially when used as electrospun fibers (Corradetti B., The Immune Response to Implanted Materials and Devices (2017); Wang et al., Materials Science and Engineering: C, (2019), 100:759-770). Additionally, electrospinning lends itself well to incorporating drugs within the fibers, providing novel drug delivery approaches (Coimbra et al., Mater Sci Eng C Mater Biol Appl, (2019), 94:86-93; Chou et al., J Mech Behav Biomed Mater, (2017), 65:724-733; Rychter et al., J Colloid Interface Sci, (2019), 536:310-327). In a preclinical guinea pig model, vancomycin-embedded electrospun coatings on middle ear prostheses reduced methicillin resistant *Staphylococcus Aureus* biofilm formation (Jang et al., Int J Pediatr Otorhinolaryngol, (2015), 79:1299-1305). Particularly relevant to applications in the laryngotracheal complex, dexamethasone incorporation into electrospun PCL has shown encouraging immunomodulation in vitro and ex vivo (Rasti et al., Iran J Pharm Res, (2019), 18:111-124; Da Silva et al., Eur J Pharm Biopharm, (2019), 142:20-30; Wang et al., J Control Release, (2020), 320:226-238).

The foregoing description of the background is provided to aid in understanding the invention, and is not admitted to be or to describe prior art to the invention.

SUMMARY OF THE INVENTION

It is to be understood that both the foregoing general description of the invention and the following detailed description are exemplary, and thus do not restrict the scope of the invention.

The capability of flocking to mimic the gecko's adhesive ability and concomitant drug delivery from both the flocks and electrospun fibers lays the framework for a technology platform with tremendous translational potential. It is shown herein that by leveraging flocking and electrospinning, a flexible, mucoadhesive patch capable of drug delivery for further use in the esophagus and laryngotracheal complex can be made.

Currently, no adhesive laryngotracheal patch has been developed with local drug release for tracheal restorative applications. In some aspects, the present invention is a bioinspired system to comprising an adhesive patch based on biocompatible polymers. In some embodiments, the polymers are commercially available but they have not been used before in this platform and for this application.

Prior art laryngotracheal wound coverage devices have been limited by complex anatomy, smooth surfaces, dynamic pressure changes and airflow during breathing. The present invention takes advantage of the idea that a bioinspired mucoadhesive patch mimicking how geckos climb smooth surfaces will permit sutureless wound coverage and also allow for drug delivery. In an exemplary embodiment, polycaprolactone (PCL) fibers were electrospun onto a planar substrate, and polyethylene glycol diacrylate (PEGDA) flocks in varying densities were formed by depositing PEGDA particles onto the PCL fibers/planar substrate to create a composite patch. A drug such as dexamethasone can be incorporated into the patch for slow release in vivo. Sample topography was assessed with laser profilometry, material stiffness with biaxial mechanical testing, and mucoadhesive testing determined cohesive material failure on porcine tracheal tissue. A degradation rate was measured over 21 days in vitro along with dexamethasone drug release profiles. Material handleability was evaluated in cadaveric larynges.

In some embodiments, polycaprolactone are dissolved in chloroform and then spun in random orientation using an electrospinning apparatus. Then, in some embodiments, the fibers can be coated with polyethylene glycol acrylate and finally polyethylene glycol powders can be "flocked" into the PEG coated PCL by a flocking machine. A polycaprolactone membranous patch can be used to attach to the mucous layer within the trachea in a sutureless manner. This material platform is capable of production in large batches permitting intra-procedural sizing by a clinician to fit the injury site. This design is also capable of sustaining anti-inflammatory drug release locally over time.

Flocking density was found to be inversely related to cohesive failure in mucoadhesive testing, with a flocking density of 2xFLK increasing failure strength to 6880±1810 Pa compared to 3028±791 in 4xFLK density and 1182±262 in xx density. The 4xFLK flocked specimens had a higher failure strength than PCL alone (1404±545 Pa) or PCL+ dipped PEG (2732±840). Flocking progressively reduced composite stiffness from 1347±15 to 763±21 N/m). Degradation rates progressed from 12% (7 days) to 16% (10 days) and 20% (21 days). Cumulative dexamethasone release at 0.4 mg/cm2 concentration was maintained over 21 days. Optimized 2xFLK density flocked patches were easy to maneuver endoscopically in laryngeal evaluation.

In another aspect, the invention relates to a mucoadhesive patch for attachment to a mucosal surface in a patient, the patch comprising a fibrous polymeric mat substrate and a plurality of polymeric flock particles that are attached to the substrate.

In some embodiments, the fibers of the polymeric mat substrate can comprise at least one of polycaprolactone (PCL), poly(lactic-co-glycolic acid (PLGA) and polymethylmethacrylate (PMMA). In certain embodiments, the fibers of the polymeric mat substrate comprise PCL.

In some embodiments, the mucoadhesive patch can incorporate a first drug to be delivered to a region of the mucosal surface. In some embodiments, the patch can exhibit sustained release of the first drug over a period of 28 days.

In some embodiments, the first drug is an anti-inflammatory drug. In some embodiments, the first drug can be a corticosteroid. In some embodiments, the corticosteroid can be dexamethasone.

In some embodiments, the first drug can be delivered at a first rate from the polymeric mat substrate of the patch and can be delivered at a second rate from the polymeric flock particles of the patch.

In some embodiments, a first drug can be incorporated into the polymeric mat substrate of the patch and a second drug can be incorporated into the polymeric flock particles of the patch.

In some embodiments, the fibers of the fibrous polymeric mat substrate can be fabricated from a monomer solution by electrospinning. In some embodiments, a drug to be delivered to a region of the mucosal surface can be included in the monomer solution prior to the electrospinning.

In some embodiments of the mucoadhesive patch, flock particles can be drawn to the substrate using an applied potential. In some embodiments, a magnitude of the applied potential can determine a concentration of the flock particles on the substrate.

In some embodiments, flock particles can be attached to the substrate by covalent crosslinking. In certain embodiments, the covalent crosslinking can be achieved by soaking the fibrous polymeric mat substrate in a monomer solution that includes a polymerization initiator, removing excess monomer solution, attaching the flock particles to the substrate using an applied potential and exposing the substrate to heat or light.

In some embodiments of the mucoadhesive patch, a monomer in the monomer solution can be identical with a monomer of which the polymeric flock particles are formed.

In some embodiments, the flock particles can comprise polyethylene glycol diacrylate (PEGDA).

In some embodiments, the inventive mucoadhesive patch can adhere sufficiently to a mucosal surface of the patient to prevent inadvertent detachment but weakly enough to permit optimization of the position of the patch.

In some embodiments, the inventive mucoadhesive patch can be flexible.

In some embodiments, the mucoadhesive patch can be capable of closing an esophageal or laryngotracheal wound in the patient.

In some embodiments, the mucosal surface can be the esophagus, larynx, trachea, oral cavity, eye conjunctiva, vagina, nasal cavity, or gastrointestinal tract of the patient.

In some embodiments, the patch comprises or is secured to the tissue with one or more sutures. Since trachea is under constant breathing forces, in some embodiments, the patch may require sutures to secure the patch inside the trachea avoiding possible aspiration of the patch into the lung.

In some embodiments, the mucoadhesive patch has a configuration and is for use in treating tracheal wall injuries.

In some embodiments, the patch is a sutureless patch that is suitable for laryngeal and tracheal anatomy with drug delivery capability. In some embodiments, the patch can be used in tracheal wall surgical restoration after injury.

In some embodiments, the patch can be used to treat tracheal stenosis. Full tracheal tissue regeneration is the main focus in the field of tracheal restoration; however, issues such as tracheal stenosis require different approaches since the major issue is related to the fibrosis formation and narrowing of the trachea. In some embodiments, the patch design enables patients and their providers to avoid drug injections and help to increase the success of tracheal dilation and stent implant.

In another aspect, the invention relates to a method of making a mucoadhesive patch for attachment to a mucosal surface in a patient, the method comprising dissolving a substrate monomer in one or more organic solvents to form a first solution of a first monomer; drawing the first monomer solution into a syringe; applying a first electrical potential as part of an electrospinning technique to form substrate fibers; forming the substrate fibers into a fibrous polymeric mat substrate; immersing the fibrous polymeric mat substrate in a second solution of a second monomer, the second solution comprising a photochemical initiator; removing excess second monomer solution by centrifugation; attaching polymeric flock particles to the substrate using a second applied electrical potential; exposing the substrate to ultraviolet light to permanently attach the polymeric flock particles to the substrate by crosslinking; and soaking the substrate in water to remove unreacted monomers and initiator. In some embodiments, the first solution further comprises a drug to be delivered to a wound.

In some embodiments, the first solution further comprises a first drug to be delivered to a region of the mucosal surface. In some embodiments, the drug to be delivered can be a corticosteroid. In certain embodiments, the drug to be delivered can be dexamethasone.

In some embodiments, the second solution comprises a drug. In some embodiments, the drug in the second solution is a second drug that is different from the first drug.

In certain embodiments, the exposing step can be followed by a step of submerging the substrate in a third solution comprising a second or third drug, then a centrifuging step to remove excess solution, wherein any of the first drug, second drug, or third drug can be the same or different.

In some embodiments, a magnitude of the second applied electrical potential can determine a concentration of polymeric flock particles attaching to the substrate.

In some embodiments, the forming step further comprises forming the polymeric mat substrate on the surface of a solid planar base.

In some embodiments, the method further comprises a step of peeling the patch from the solid planar base.

In some embodiments, the polymeric flock particles are polyethylene glycol diacrylate (PEGDA) particles and the second monomer is PEGDA.

In some embodiments, the substrate fibers form a polymeric mat substrate on the surface of a solid planar base. In some embodiments, the mucoadhesive patch is flexible and can be peeled from the solid planar base.

In some embodiments, the first monomer can be selected from the group consisting of polycaprolactone (PCL), poly (lactic-co-glycolic acid (PLGA) and polymethylmethacrylate (PMMA). In certain embodiments, the first monomer can be PCL.

In another aspect, the invention relates to a method of treating a disease or condition in a subject in need thereof, comprising administering to a mucosal surface of the subject, an effective amount of the mucoadhesive patch of the invention. In some embodiments, the patch is administered to an esophageal or laryngotracheal mucosal surface. In some embodiments, the patch is applied to a wound. In some embodiments, the mucoadhesive patch closes the wound.

In some embodiments, the invention relates to a method of delivering a drug to a region of a mucosal surface of a patient in need thereof, the method comprising applying to the mucosal surface the mucoadhesive patch as described above, the mucoadhesive patch incorporating an effective amount of a drug to be delivered. In some embodiments, the drug is released in a controlled manner. In some embodiments, the drug release is sustained over a period of time. In some embodiments, the drug release is characterized by a burst or immediate release. In some embodiments, the drug release is delayed release. In some embodiments, an amount of drug delivered at a given time correlates with a concentration of flock particles attached to the substrate.

It is to be understood that both the foregoing general description and the following detailed description are exemplary, and thus do not restrict the scope of the invention. Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION

Translational implementation of novel materials and therapeutic delivery systems are needed for the management of laryngotracheal and esophageal wounds. Current best practice suggests an instrumental role for intralesional and in-office steroid injection in subglottic and tracheal stenosis. Wierzbicka, et al., *The efficacy of submucosal corticosteroid injection and dilatation in subglottic stenosis of different aetiology*, Journal of Laryngology and Otology 2016, 130: 674-679; Hoffman, et al., *Serial office-based steroid injections for treatment of idiopathic subglottic stenosis*, Laryngoscope 2017, 127: 2475-2481; Franco, et al., *Awake serial intralesional steroid injections without surgery as a novel targeted treatment for idiopathic subglottic stenosis*, Laryngoscope 2018, 128:610-617. These interventions appear to reduce disease progression and increase the duration of time between repeat procedures. Despite the compelling evidence for the effectiveness of steroid injections, application of corticosteroids to the stenotic region are limited by the practical aspects of performing an in-office injection involving flexible videolaryngoscopy and a transcutaneous injection. Franco, et al., supra. The inventive novel patch could allow for continuous drug delivery across the desired surface, filling an as yet unmet clinical need. In addition to expanding the dose and duration possible for steroid treatment, the inventive patch treatment could reduce the currently necessary in-office steroid injections. Similarly, few effective adjuvant therapies are available for glottic webs outside of keels and stents that remain largely unchanged over the past couple of decades. Fussey, et al., *Surgical management of acquired anterior glottic web: a systematic review*, Journal of Laryngology and Otology 2019: 1-8. Interest in improved management of these webs is evidenced by a recent study exploring bovine pericardium as a possible new graft material and more advanced surgical closure techniques. Zapater, et al., *Use of bovine pericardium for the treatment of anterior iatrogenic glottic web*, Laryngoscope 2019, 129: 2121-2124; Yilmaz, *Surgical treatment of glottic web using butterfly mucosal flap technique: experience on 12 patients*, Laryngoscope 2019, 129: 1423-1427.

Figure 1:
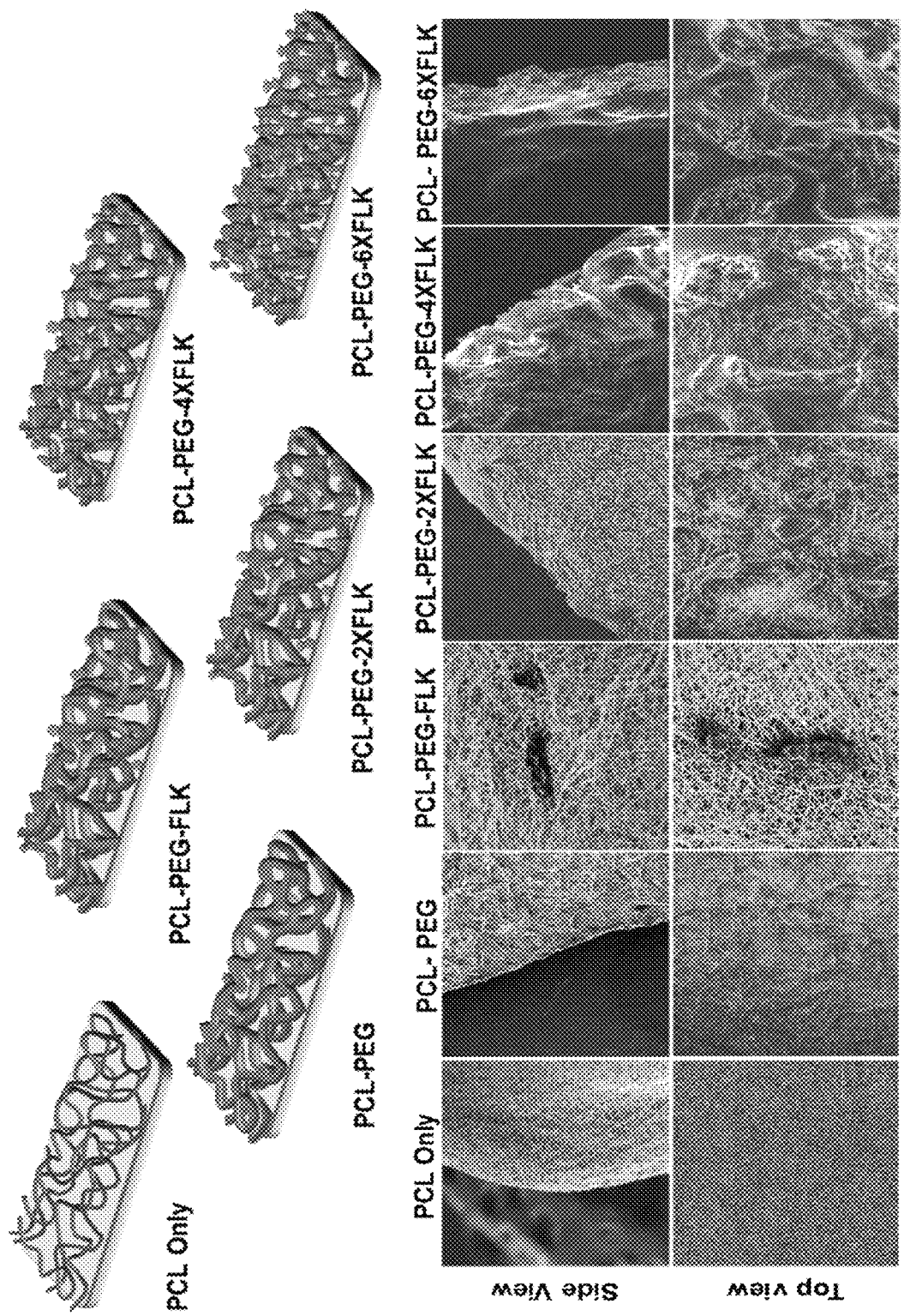
FIG. 1. Schematic representation and scanning electron micrography of the six patch designs developed. The base electrospun PCL fiber patch was coated in PEG to form the PCL-PEG substratum. Upon this substratum, flocking was performed to add 4 increasing densities of PEG flocks, which were then labelled PCL-PEG-FLK, PCL-PEG-2XFLK, PCL-PEG-4XFLK and PCL-PEG-6XFLK to denote increasing relative concentration of surface flocks. Scanning Electron Microscopy was conducted on coated dry samples under 20 KV and micrographs are presented from top and side views. The scale bar represents 100 μm.
Figure 2:
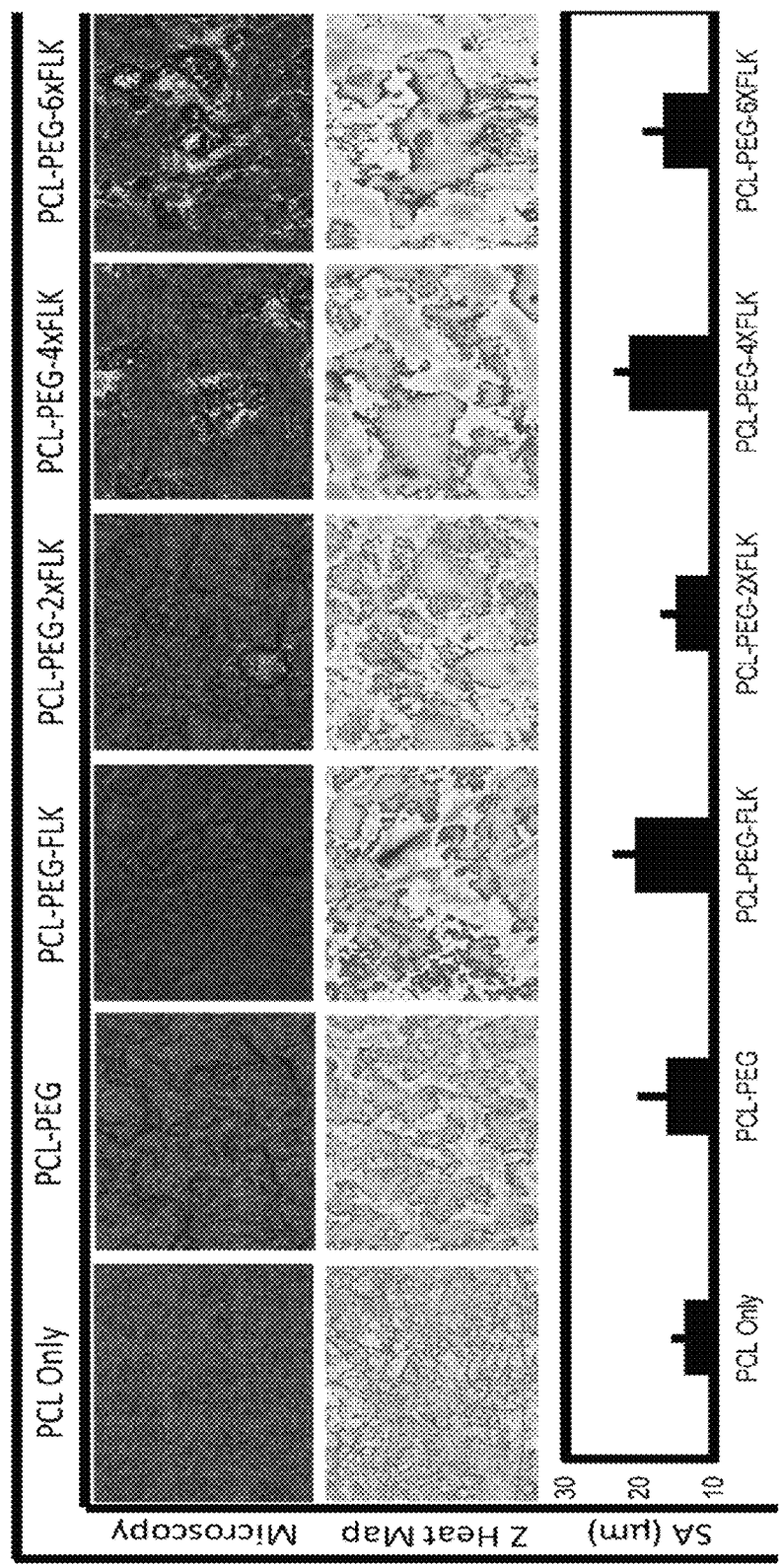
FIG. 2. Laser Profilometry to measure surface features. (A) Microscopy images of the 2 mm×1.5 mm rectangular areas visualized in the optical scan. (B) Heat maps generated from the laser profilometry showing high peaks in red and base substrate in deep blue. (C) Surface arithmetical mean height (SA) measured for each group (n=6). SA shows the difference between the heights of each point compared to the arithmetical mean of the samples' surface. According to the results, the data showed no significant SA results.
Figure 4:
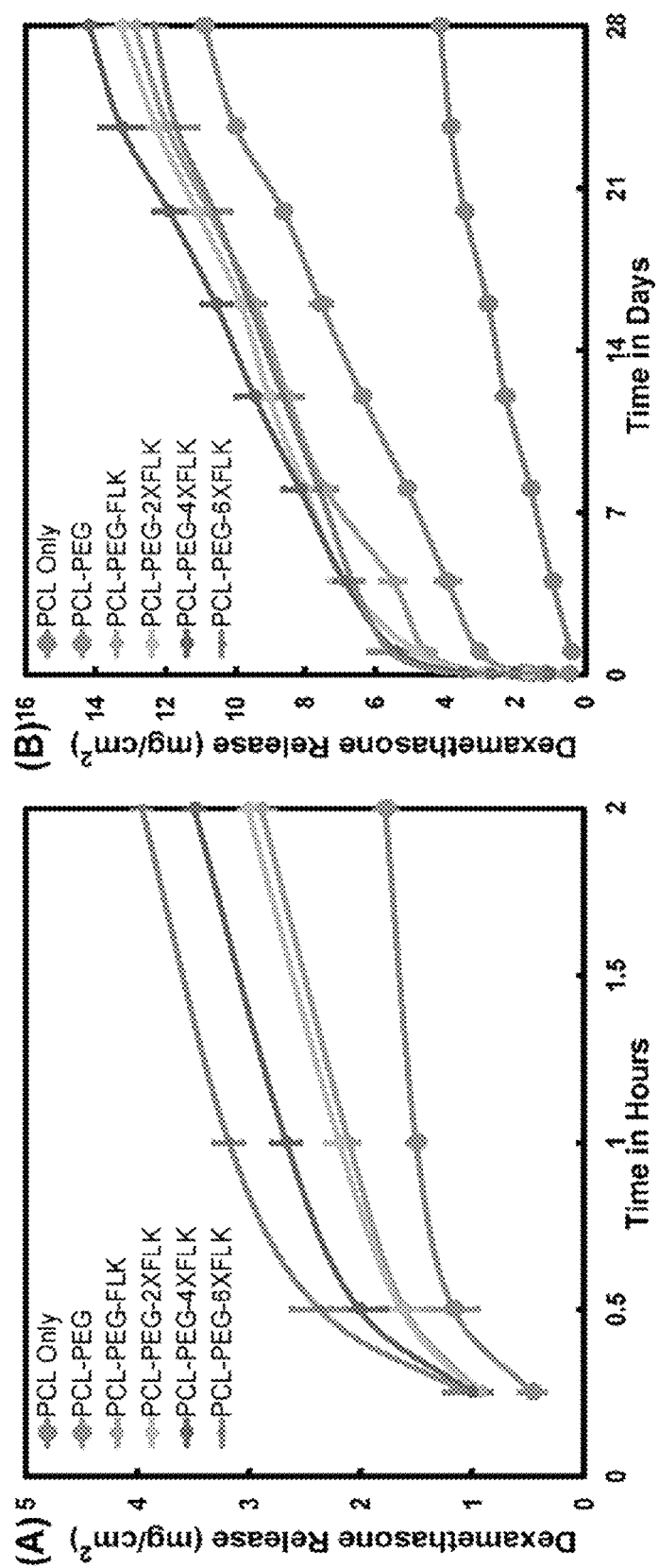
FIG. 4. Dexamethasone release from the patches over 28 days. Dexamethasone release was measured for each group (A) every half hour over the first 2 hours, to evaluate burst release behavior and (B) then at days 1, day 4 and every 4 days to day 28 to evaluate sustained release. No measurable release was observed from the PCL Only group over the first 2 hours, and no significant difference were found between these groups over the 2 hour burst release period. At Days 4 and 8, the PCL-PEG-2XFLK, PCL-PEG-4XFLK and PCL-PEG-6XFLK showed significantly greater release than the PCL Only and PCL-PEG groups (p<0.001), at days 12 and 16, the PCL only group showed significantly lower release than all FLK groups (p<0.001), and at days 20, 24 and 28, the PCL only group showed significantly lower release than all other groups (p<0.01).
Figure 5:
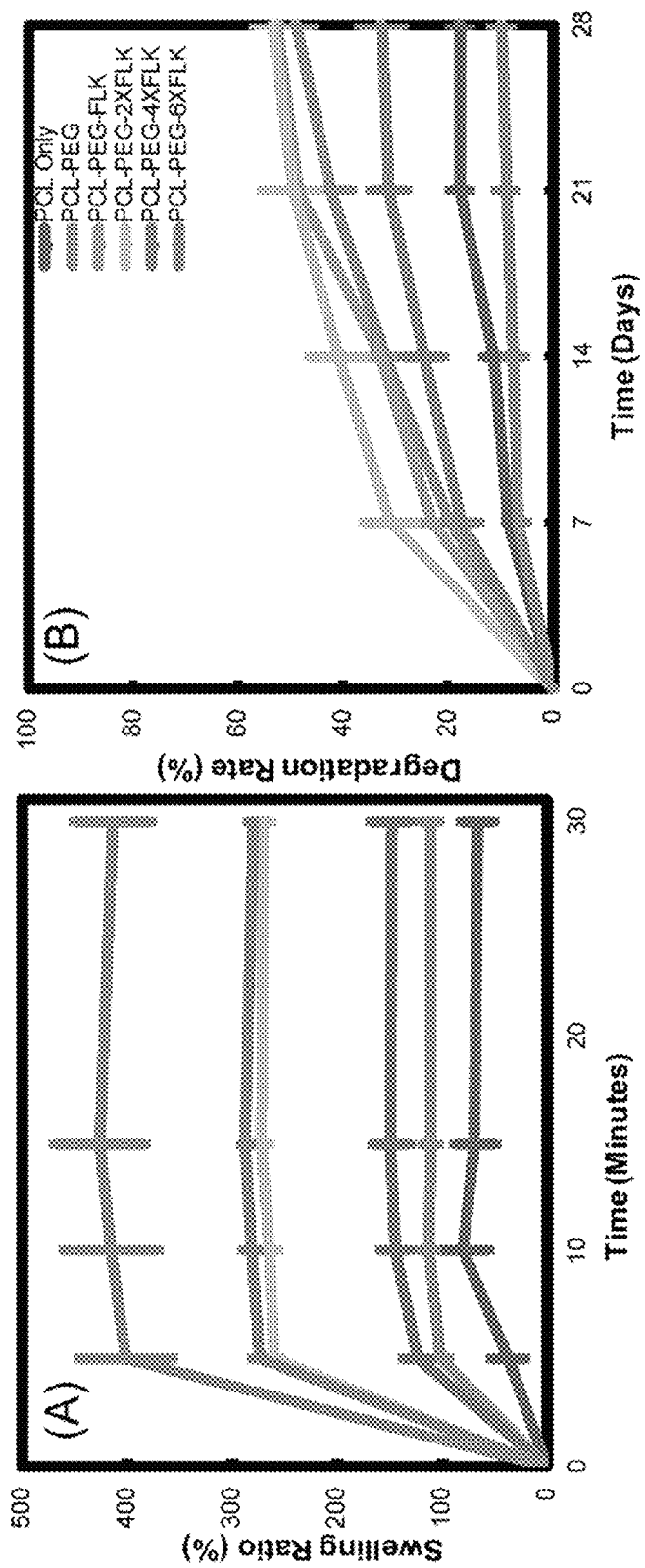
FIG. 5. (A) Swelling behavior. Swelling ratio of patches in PBS (at room temperature) over time. The water absorbency was measured every 5 minutes until the samples reached the swelling equilibrium. (B) Material degradation over time. Material degradation of each group was measured over a 28 day period and all groups stabilized after the initial degradation within the first 7 days, such that there was a main effect of the 21 and 28 day time points being significantly different from the 0 and 7 day time points across all groups (p<0.05). Degradation was significantly lower in the PCL only and PCL-PEG-6XFLK groups compared to other groups, such that their degradation was significantly lower compared to the PCL-PEG-FLK and PCL-PEG-2XFLK groups for all time points day 7 and later, and compared to all other groups at day 14 and later (p<0.03).
Figure 6:
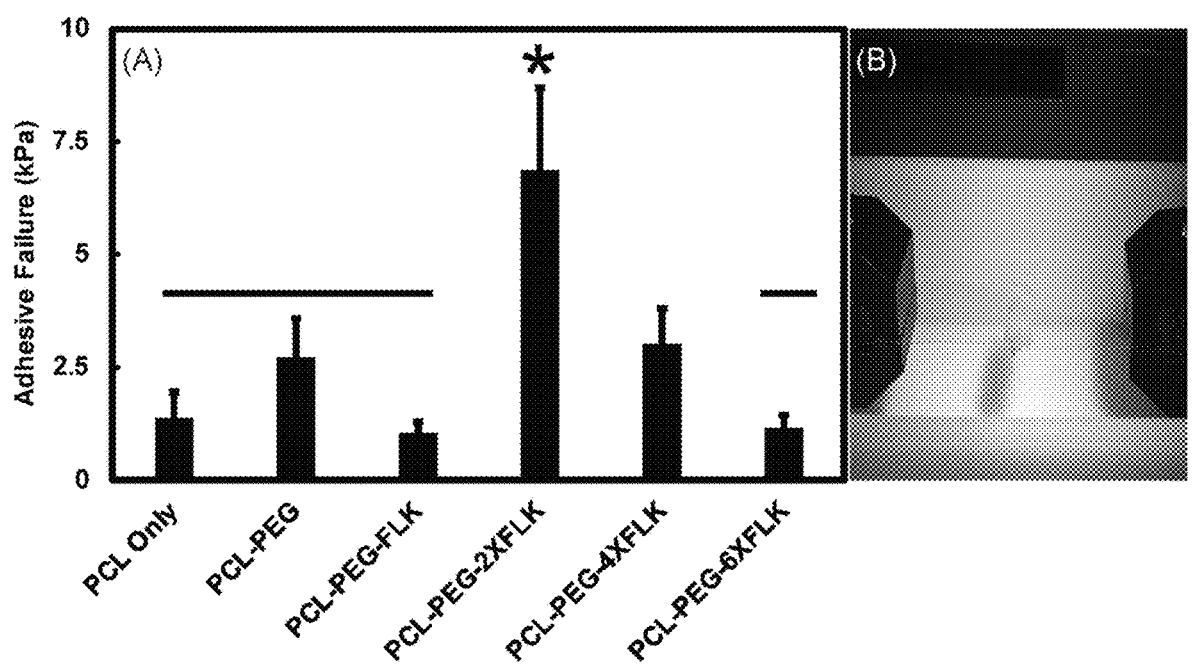
FIG. 6. Mucoadhesion testing. (A) Mucoadhesion testing was performed for all materials against a hydrated tracheal surface with intact mucosa in lap shear mode. It was found that the PCL-PEG-2XFLK group demonstrated significantly greater (* indicates significantly different at p<0.05) stress at adhesive failure compared to all groups except PCL-PEG-4XFLK (different from PCL-PEG-4XFLK at p=0.09). (B) Mucoadhesion experiment on fresh porcine trachea conducted using single lap shear protocol. Patches were connected to fixturing on the UStretch machine and the trachea specimens were attached to the actuator. The experiment was conducted at a strain rate of 10 mm/min.
Figure 7:
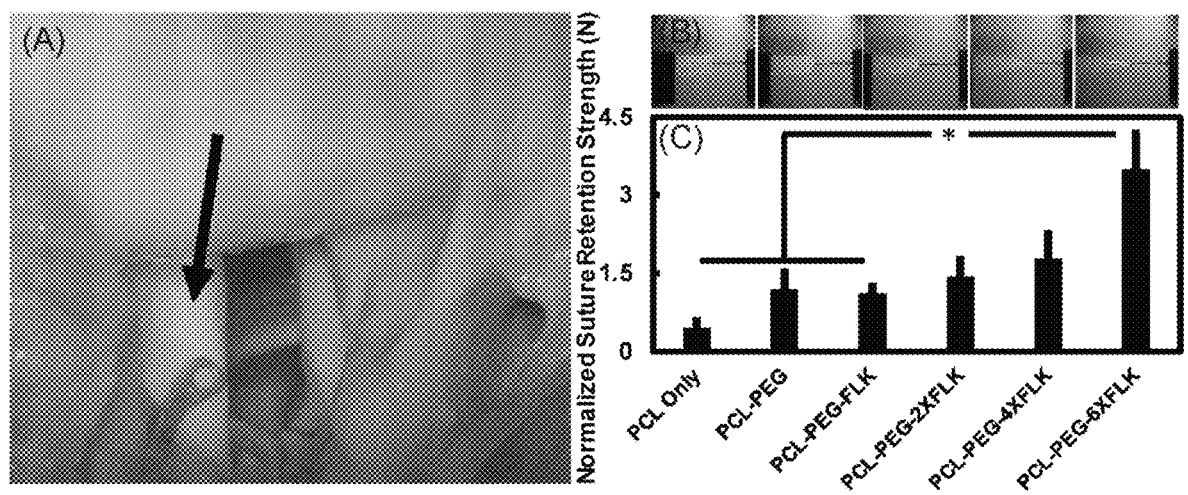
FIG. 7. A) In situ adhesion in a cadaver model and suturability properties. In-procedure imaging of the prepared flocked patch (PCL-PEG-2XFLK) adhering to the vocal fold area of the larynx. (B) Top views of patch failure in suture retention experiment. Circumferential tearing pattern and crack propagation were observed during progression of the test, to breakage. (C) Suture retention strength. Failure strength of the suture measured in the PCL-PEG-6XFLK was significantly higher than PCL only, PCL-PEG, PCL-PEG-FLK (p<0.025).

The accompanying Figures illustrate embodiments of the present invention, which makes use of the same principle of adhesion that geckos use when climbing up vertical surfaces. FIG. 1 illustrates the overall structures of possible patch embodiments, including various patch configurations and layouts. FIG. 2 shows visualization of patch surfaces using laser profilometry. FIG. 4 shows profiles of timed release of a drug obtainable with the inventive patch, the representative drug being dexamethasone. FIG. 6 shows mechanical properties of an exemplary inventive patch, as compared with the corresponding properties of porcine tracheal mucosa. FIG. 5 shows that an amount of flock particles incorporated into the inventive patch can be optimized to produce high mucoadhesive strength, but high mucoadhesive strength can come at the price of an increased degradation rate. FIG. 7 shows a practical application of the inventive patch wherein a flexible patch is placed over the left vocal fold of a cadaveric larynx.

Similar to other studies quantifying mucoadhesion of flocked materials, surface contact area and shape appear to play a large role in final adhesive forces. Tamelier, et al., *Millimeter size patch behavior of gecko-inspired reversible adhesive*, Sensors IEEE 2011: 1819-1822. Furthermore, data suggest that preload plays a crucial role in the ultimate adhesive properties. In the evaluation presented in the present examples, all samples had an equivalent preload force/time prior to quantification. The improved cohesive adhesion in the 2xFLK found in the present study can be attributed to an optimized concentration of flocks leading to mechanical interlocking between the flocks and mucin layer of the porcine trachea wall. Conversely, the 4xFLK and 6xFLK groups have higher flock concentrations, and the lower adhesion properties in these groups could be related to a decreased available surface area for adherent surface to interact with the flocks. In addition, there is some evidence that roughness plays a role in the mucoadhesive properties. Id. It is likely that the mucosa—material interaction is multifactorial, with contributions from moisture, surface roughness, and surface area/shape. This is supported by the multitude of factors found to contribute to the gecko's ability to adhere to surfaces using the setae on its legs, ranging from water contact angle, van der waals forces, capillary forces, and geometry. Autumn, *Properties, principles, and parameters of the gecko adhesive system*, in Smith, A. M.; Callow, J. A., eds., *Biological Adhesives*, Berlin: Springer, 2006, pp. 225-256. The differences in roughness measured and inherent to the varying patch designs in our study allowed for selection of the optimal design. Both the roughness and surface contact area varied with the density of flocks. As shown in FIG. 2, no or a very low density of flocks resulted in a low adhesive force that increased and then decreased again at higher densities.

The adhesive properties of the inventive patch are particularly valuable in the moist environment found in the trachea and esophagus. In particular, sufficient mucoadhesion is necessary for efficient drug delivery and has been assessed for optimizing approaches and therapeutics. Pendekal, et al., *Formulation and evaluation of a bioadhesive patch for buccal delivery of tizanidine*, Acta Pharmaceutica Sinica B 2012, 2: 318-324; Shaikh, et al., *Mucoadhesive drug delivery systems*, J. Pharm. Bioallied Sci. 2011, 3: 89-100. To date, drug delivery patches have not proved an effective route of predictably delivering corticosteroids to the local tissue. In the nasal cavity, a dexamethasone stent shows promise in modulating wound healing. Beule, et al., *Effects of topically applied dexamethasone on mucosal wound healing using a drug-releasing stent*, Laryngoscope 2008, 118: 2073-2077. The inventive novel flocked patch effectively delivered a sustained release of corticosteroid over the course of 21 days while also allowing for an initial burst release of steroid. The initial fast burst release observed during the first 2 hours may be related to a higher volume of PEGDA flocks in the patch. Also, the presence of flocks caused higher drug release compared to the PCL-PEGDA, explaining the impact of flocks on the uptake and the release of the dexamethasone from the patches.

Critically, the study was limited to in vitro, ex vivo, and cadaveric testing. The initial design precluded longer duration degradation and drug delivery tests. Though, practically, most patches or stents, if not bioresorbable, are typically removed 10-14 days after placement, as also occurs with keels and glottic web treatments. Mucoadhesion testing was performed on excised porcine trachea with a reasonably reproducible in vivo preload force. However, the trachea microenvironment in vivo varies from the ex vivo counterpart with increased local temperature, mucocilliary function, and a separate local microbiome. These variables may confer additional adhesion based on the functional design of the flocked patch, though in vivo studies are needed to quantify differences. Similarly, outside of studies with an intranasal dexamethasone stent, optimal concentration for continuous delivery of steroid to laryngotracheal and esophageal wounds remains unknown. Despite these limitations, the in vivo, ex vivo, and cadaveric testing of the self-adhering patch permitted design optimization and preparation for preclinical and clinical testing for translation application.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the DETAone or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

In some embodiments, the invention provides a mucoadhesive patch for attachment to a mucosal surface in a patient, the patch comprising a fibrous polymeric mat substrate and a plurality of polymeric flock particles that are attached to the substrate.

In another embodiment, the invention provides a method of treating a disease or condition in a subject, comprising administering to a mucosal surface of the subject an effective amount of a mucoadhesive patch as described herein. In some embodiments, the patch is administered to treat an esophageal or laryngotracheal disease or condition in the subject. In some embodiments, the patch is administered to treat a wound or injury. In some embodiments, the patch is administered to close a wound. In some embodiments, the patch is administered to facilitate wound healing. In some embodiments, the patch is administered to treat tracheal stenosis. In some embodiments, the patch is administered following surgery.

In another embodiment, the invention provides a method of delivering a drug to a region of a mucosal surface of a patient in need thereof, comprising applying to the mucosal surface a mucoadhesive patch as described herein. In some embodiments, an amount of drug delivered at a given time correlates with a concentration of flock particles attached to the substrate.

As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition, but may not be a complete cure of the disease and/or condition.

For the present purposes, a "drug" is a medicine or substance that exerts a physiological effect when ingested or otherwise introduced into the body of a patient.

"Electrospinning" is a method of producing polymeric fibers in which an electrical potential applied to charged polymer threads or polymer melts causes fiber diameters to increase.

A "mucosal surface" is a surface of the body of a patient that is characterized by the presence of an overlying mucosal fluid, for example saliva, tears, or nasal, gastric, cervical, or bronchial mucus.

The terms "treating" and "treatment" as used herein refer to administering to a subject a therapeutically effective amount of an agent so that the subject has an improvement in the disease or condition. The improvement is any observable or measurable improvement. Thus, one of skill in the art realizes that a treatment may improve the patient's condition, but may not be a complete cure of the disease or condition. Treating may also comprise treating subjects at risk of developing a disease and/or condition.

The inventive mucoadhesive patches can be attached to mucosal surfaces in patients in ways that are not particularly limiting. In some embodiments, the patches are useful for purposes of reinforcement or closing wounds or openings in those mucosal surfaces. Mucosal surfaces are typically moist, being characterized by the presence of an overlying mucosal fluid. The overlying mucosal fluid can include but is not limited to saliva, tears, and nasal, gastric, cervical, or bronchial mucus. Targeted mucosal surfaces can include but are not limited to the esophagus, larynx, trachea, bronchi, oral cavity, tongue, eye conjunctiva, ears, nose, vagina, endometrium, urethra, anus, nasal cavity, or gastrointestinal tract of the patient.

The inventive mucoadhesive patches are especially useful for their additional ability to incorporate drugs and to release them from the patches at predictable rates. The fibrous polymeric mat substrate and the polymeric flock particles can separately incorporate one or more drug materials, if desired, which can then be released from the patch, with substrate and flock particle portions releasing materials at the same or different rates. In some embodiments, the release is controlled, sustained, delayed or can be characterized by a burst release. In some embodiments, the release kinetics can be characterized by a burst release, followed by a more slow and sustained release over time.

Drugs that can be usefully incorporated into the inventive mucoadhesive patches include but are not limiting. In some embodiments, one or more anti-inflammatory drugs are incorporated. In some embodiments, one or more antibiotics are incorporated. In some embodiments, a combination of drugs can be incorporated, such as one or more anti-inflammatory drugs and one or more antibiotics. In some embodiments, the anti-inflammatory drug is a corticosteroid and/or corticoids including alclometasone aldosterone, dipropionate, aldosterone, amcinonide, beclometasone, beclomethasone dipropionate, betamethasone, betamethasone dipropionate, betamethasone valerate, budesonide, chloroprednisone, ciclesonide, clobetasol propionate, clobetasone butyrate, clocortolone, cloprednol, corticosterone, cortisol, cortisone, cortisone acetate, cortivazol, deflazacort, 11-dehydrocorticosterone, 11-deoxycorticosterone, 11-deoxycortisol, 21-deoxycortisol, 21-deoxycortisone, desonide, dexamethasone, deoxycorticosterone, desoximetasone, diflorasone, difluocortolone, difluprednate, 17α,21-dihydroxypregnenolone, fluclorolone, fluclorolone acetonide, fludrocortisone, flugestone, flumetasone, flunisolide, fluocinolone, fluocinonide, fluocortin, fluocortolone, fluorometholone, fluperolone, fluprednidene acetate, fluprednisolone, fluticasone, fluticasone furoate, fluticasone propionate, formocortal, halcinonide, halometasone, hydrocortisone (cortisol), hydrocortisone aceponate, hydrocortisone acetate, hydrocortisone buteprate, hydrocortisone butyrate, hydrocortisone valerate, 18-hydroxycorticosterone, 18-hydroxy-11-deoxycorticosterone, 11β-hydroxypregnenolone, 17α-hydroxypregnenolone, 21-hydroxypregnenolone, 11β-hydroxyprogesterone, 18-hydroxyprogesterone, 17α-hydroxyprogesterone, 11-ketoprogesterone, loteprednol, medrysone, meprednisone, methylprednisolone, mometasone, mometasone furoate, paramethasone, prebediolone acetate, prednicarbate, prednisolone, prednisone, pregnenolone, prednylidene, progesterone, rimexolone, RU-28362, tixocortol, tixocortol pivalate, triamcinolone, triamcinolone acetonide, 11β,17α,21-trihydroxypregnenolone, ulobetasol, and derivatives thereof; steroids including but not limited to androstanolone, conjugated estrogens, desogestrel, drospirenone, estradiol, estradiol acetate, estradiol hemihydrate, estropipate, ethinylestradiol, etonogestrel, fluoxymesterone, levonorgestrel, medroxyprogesterone acetate, methyltestosterone, norethisterone acetate, oxandrolone, oxymetholone, testosterone, and derivatives thereof. In some embodiments, the drug is an antihistamine, which can include but is not limited to acrivastine, alimemazine, amoxapine, azelastine, bilastine, bromodiphenhydramine, brompheniramine, buclizine, carbinoxamine, cetirizine, chlorodiphenhydramine, chlorpheniramine, chlorpromazine, chlorprothixene, chloropyramine, cimetidine, cinnarizine, clemastine, clomipramine, clozapine, cyclizine, cyproheptadine, desloratadine, dexchlorpheniramine, dimenhydrinate, dimetindene, diphenhydramine (Benadryl), dosulepin, doxepin, doxylamine, ebastine, embramine, famotidine, fexofenadine, hydroxyzine, imipramine, ketotifen, lafutidine, levocabastine, levocetirizine, levomepromazine, loratadine, maprotiline, meclizine, mianserin, mirtazapine, nizatidine, olanzapine, olopatadine, orphenadrine, periciazine, phenindamine, pheniramine, phenyltoloxamine, promethazine, pseudoephedrine, pyrilamine, quetiapine, ranitidine, roxatidine, rupatadine, tiotidine, trazodone, tripelennamine, triprolidine, and derivatives thereof. A variety of other drugs can be included such as, for example, amoxicillin, cephalexin, clonidine, cyanocobalamin, epinephrine (adrenaline), glipizide, 5-hydroxytryptophan, insulin, insulin analogues such as insulin aspart or insulin glargine, leuprolide, methylphenidate, nifedipine, nitroglycerin, octreotide, oxymetazoline, oxytocin, propranolol hydrochloride, ramipril, rantidine hydrochloride, repaglinide, rivastigmine, salbutamol, simvastatin, scopolamine, thyrotropin-releasing hormone (TRH), vitamin B12 and derivatives thereof.

Additional materials and drugs that can be delivered with bioadhesive patches include but are not limited to nicotine, 5-aminolevulinic acid (5-ALA) and derivatives thereof, antibiotics, parasympatholytics, cholinergics, neuroleptics, antidepressants, antihypertensives, photosensitisers, photosensitiser precursors, sympathomimetics, sympatholytics and antisympathotonics, antiolytics, local anaesthetics, central analgesics, antirheumatics, coronary therapeutics, hormones, antihistamines, prostaglandin derivatives, vitamins, nutrients and cytostatics. See McCarron, et al., US 2017/0340580 A1.

The inventive mucoadhesive patch can be useful for delivering chemotherapeutics and anti-cancer/anti-tumor agents including but not limited to 5-fluorouracil, chlorambucil, aminolevulinic acid, altretamine, ambomycin, vincristine, buthionine sulfoximine, asparaginase, bleomycin, busulin, trimetrexate, adriamycin, taxotere, carboplatin, cispiatin, carmustine, cladribine, 5-ethynyluracil, 9-dihydrotaxol, mitomycin, abiraterone, acivicin, teniposide, aclarubicin, acodazole hydrochloride, canarypox IL-2, acronine, thioguanine, acylfulvene, adecypenol, adozelesin, aldesleukin, thiotepa, ambamustine, busulfan, ametantrone acetate, amidox, amrubicin, mercaptopurine, cyclophosphamide, cytarabine, paclitaxel, pentostatin, dacarbazine, dactinomycin, daunorubicin, camptothecin derivatives, doxorubicin, etoposide, fludarabine phosphate, hydroxyurea, BRC/ABL antagonists, breflate, brequinar sodium, bropirimine, budotitane, amifostine, actinomycin, calcipotriol, calphostin C, calusterone, caracemide, carbetimer, floxuridine, idarubicin, ifosfamide, lomustine, mechlorethamine, melphalan, methotrexate, mitoxantrone, pliamycin, procarbazine, streptozocin and vinblastine. See Hsu, US 2016/0045158 A1. Hsu also describes the use of transdermal drug delivery methods such as a patch to deliver vaccine antigens, a variety of hormones, agents for the treatment of diabetes mellitus and numerous other drugs. The disclosure of Hsu is hereby incorporated by reference in its entirety.

Methods of making the inventive mucoadhesive patches are not particularly limiting and can take advantage of the vast experience of many researchers in assembling scaffolds for tissue engineering using polycaprolactone (PCL) fibers prepared using an electrospinning technique. Cipitria, et al., *Design, fabrication and characterization of PCL electrospun scaffolds—a review*, J. Materials Chem. 2011, 21: 9419-9453. There are numerous parameters to adjust in order to produce the desired electrospun fibrous PCL meshes from a first solution of a first monomer using a first applied electrical potential. Polymeric fibers of other compositions can also be used. Poly(lactic-co-glycolic) acid (PLGA), polymethylmethacrylate (PMMA), polylactic acid (PLA), polyglycolic acid (PGA), poly(caprolactone), diol/diacid aliphatic polyester, polyester-amide/polyester-urethane, poly(valerolactone), poly(hydroxyl butyrate), polybutylene terephthalate (PBT), polyhydroxyhexanoate (PHH), polybutylene succinate (PBS), poly(hydroxyl valerate), polyethylene oxide (PEO), polyethylene glycol (PEG), collagen, fibronectin, keratin, polyaspartic acid polylysine, chitin, silk fibroin, pectin, polycaprolactone, polyhydroxyalkanoates, dextrans, and polyanhydrides have been found to be useful in tissue scaffold construction. See Kuo, et al., US 2011/0293685 A1, which is hereby incorporated by reference in its entirety, and references therein. The fibers are formed into a polymeric mat substrate. This can be done in any suitable way, e.g., by laying the fibers out on a solid planar base, such as a glass slide or a plastic sheet, or by pressing between two planar and parallel solid surfaces.

Making polymeric fibers by electrospinning for use as biocompatible structural elements has been widely explored. See, e.g., Johnson, Fiber scaffolds for use in esophageal prostheses, U.S. Pat. No. 10,227,568 B2; Johnson, Fiber scaffolds for use in tracheal prostheses, WO 2013/078051 A1, Yang, et al., Macroporous 3-D scaffolds for tissue engineering, and U.S. Pat. No. 9,402,710 B2, which are hereby incorporated by reference in their entireties. This general area has recently been reviewed. Nikolova, et al., *Recent advances in biomaterials for 3D scaffolds: a review*, Bioact. Mater. 2019: 271-292; and Chen, et al., *Electrospinning: an enabling nanotechnology platform for drug delivery and regenerative medicine*, Advanced Drug Delivery Reviews 2018, 132: 188-213 which are hereby incorporated by reference in their entireties.

The fibrous polymeric mat substrate can then be immersed in a second solution of a second monomer, followed by removal of excess monomer solution by centrifugation. Polymeric flock particles can then be attached to the polymeric mat substrate by applying a second electrical potential. Flocking technology, the science of applying short fibers almost vertically on a substrate that is coated with a flocking adhesive, is well known and has been extensively practiced in the textile industry. Walther, et al., *Development of novel scaffolds for tissue engineering by flock technology*, Textile Research Journal 2007, 77(11): 892-899. In the present context, the polymeric flock particles can advantageously correspond to the second monomer and can have mucoadhesive properties. Suitable mucoadhesive polymeric materials can include but are not limited to polyethylene glycol diacrylate (PEGDA), cyanoacrylates, polyacrylic acid, sodium carboxymethylcellulose, hyaluronic acid, hydroxypropylcellulose, polycarbophil, chitosan, gellan, copolymer of methyl vinyl ether, hydroxypropylmethylcellulose (HPMC), sodium carboxymethylcellulose, carbopol-934P and Eudragit RL-100, thiolated poly(acrylic acid), poloxamer, celluloseacetophthalate, methyl cellulose, hydroxy ethyl cellulose, poly(amidoamine) dendrimers, poly(dimethyl siloxane), poly(vinylpyrrolidone). mucin, gelatin, polycarbophil, poloxamer, alginate, poly(methacrylic acid), sodium carboxymethyl cellulose and derivatives thereof. See Boddupalli, et al., *Mucoadhesive drug delivery system: an overview*, J. Adv. Pharm. Tech. & Res. 2010, 1(4): 381-387, page 385. Other suitable mucoadhesive polymeric materials can include but are not limited to hydroxypropyl methylcellulose (HPMC), carbapol, ethylcellulose, methylcellulose, Eudragit RS-100, guar gum, Carbopol 940P, Carbopol 934P, sodium carboxymethylcellulose, xanthan gum and derivatives thereof. See Navita, et al., *Mucoadhesive microspheres: a review*, J. Drug Delivery & Therapeutics 2014, 4(5): 48-54, page 52. Other suitable mucoadhesive polymeric materials can include but are not limited to polylactic acid and copolymers, polyvinyl acetate, celluloses and derivatives (such as carboxymethyl cellulose, cellulose acetate, cellulose acetate propionate, ethyl cellulose, hydroxypropyl methyl cellulose, hydroxyalkyl methyl celluloses and alkyl celluloses), crosslinked dextrans, polyethylene glycol, diethylaminoethyl dextran, poly(cyanoacrylates), copolymers of poly(ethylene glycol) (PEG) and poly(lactic acid) (PLA), poly(lactic-co-glycolic acid), poly (ortho esters), hydrogels, polyethylene glycol caprylic/capric glycerides; vinyl polymers (e.g., polyhydroxyethyl acrylate, polyhydroxyethyl methacrylate, polyvinyl alcohol and polyvinyl pyrrolidone). See Hsu, US 2016/0045158 A1.

Flocking technology is well known in the textile industry for its ability to impart adhesive qualities to a fabric. See, e.g., Merovitz, Electrostatic flocking and articles made therefrom, U.S. Pat. No. 7,897,236 B2; Newman, Method of producing flocked nonwoven fabric, U.S. Pat. No. 3,459,579; Abrams, Flocked articles and methods of making same, U.S. Pat. No. 7,351,368 B2 and references therein; Jorro de Inza, et al., Inner flock coating for vehicles with indicative and/or decorative motif and its manufacturing process, U.S. Patent Appl. Pub. No. 2013/0276953 A1; Abrams, Flocked multi-colored adhesive article with bright lustered flock and methods for making the same, U.S. Pat. No. 8,007,889 B2.

In some embodiments, once electrostatic or other flocking technology has been used to orient the flocking particles or fibers into a generally perpendicular relationship with the polymeric mat substrate, the adhesive comprised by the second monomer can then be cured to permanently attach the flock particles to the substrate. Those skilled in the art would understand that, with a photoinitiator present, the second monomer can be polymerized and crosslinked to fix the flock particle positions by application of ultraviolet light. Alternatively, other means of curing such as heat or radiation can be used.

In some embodiments, advantageously, one or more drugs can be incorporated into either the polymeric mat substrate or the flock particles of the inventive mucoadhesive patch by soaking either the polymeric mat substrate or the flocked substrate in a solution of the drug. The inventive patch can thus be prepared in such a way that the same or different drugs are released from the substrate fibers and the flock particles and in such a way that drug release from the substrate fibers and the flock particles occurs at the same or different rates. Techniques are available to engineer these polymeric matrices so as to define a rate of drug release. See, e.g., Hardy, et al., The use of pvp to control the release profile of an active ingredient from a hydrophilic polymer matrix tablet, WO 2008/004001 A2; Jeong, et al., Method of manufacturing porous matrix-type controlled release systems using emulsion technique, U.S. Pat. No. 6,451,348 B1; Li, et al., Controlled drug delivery, U.S. Pat. No. 9,744,272 B2; Sibambo, et al., Monolithic drug delivery system, U.S. Patent Appl. Pub. No. 2010/0068169 A1; Badwan, et al., Universal controlled-release composition, U.S. Patent Appl. Pub. No. 2005/0074491 A1.

In another embodiment, the invention provides a method of making a mucoadhesive patch for attachment to a mucosal surface in a patient, the method comprising:
  dissolving a substrate monomer in one or more organic solvents to form a first solution of a first monomer;
  drawing the first monomer solution into a syringe;
  applying a first electrical potential as part of an electrospinning technique to form substrate fibers;
  forming the substrate fibers into a fibrous polymeric mat substrate;
  immersing the fibrous polymeric mat substrate in a second solution of a second monomer, the second solution comprising a photochemical initiator;
  removing excess second monomer solution by centrifugation;
  attaching polymeric flock particles to the substrate using a second applied electrical potential;
  exposing the substrate to ultraviolet light to permanently attach the polymeric flock particles to the substrate by crosslinking; and
  soaking the substrate in water to remove unreacted monomers and initiator.

In some embodiments, the first solution further comprises a first drug to be delivered to a region of the mucosal surface. In some embodiments, the drug to be delivered can be a corticosteroid. In certain embodiments, the drug to be delivered can be dexamethasone.

In some embodiments, the second solution comprises a drug. In some embodiments, the drug in the second solution is a second drug that is different from the first drug.

In certain embodiments, the exposing step can be followed by a step of submerging the substrate in a third solution comprising a second or third drug, then a centrifuging step to remove excess solution, wherein any of the first drug, second drug, or third drug can be the same or different.

In some embodiments, a magnitude of the second applied electrical potential can determine a concentration of polymeric flock particles attaching to the substrate.

In some embodiments, the forming step further comprises forming the polymeric mat substrate on the surface of a solid planar base.

In some embodiments, the method further comprises a step of peeling the patch from the solid planar base.

In some embodiments, the polymeric flock particles are polyethylene glycol diacrylate (PEGDA) particles and the second monomer is PEGDA.

In some embodiments, the substrate fibers form a polymeric mat substrate on the surface of a solid planar base. In some embodiments, the mucoadhesive patch is flexible and can be peeled from the solid planar base.

In some embodiments, the first monomer can be selected from the group consisting of polycaprolactone (PCL), poly (lactic-co-glycolic acid (PLGA) and polymethylmethacrylate (PMMA). In certain embodiments, the first monomer can be PCL.

In some aspects, the inventive mucoadhesive patches offer numerous advantages over traditional methods of treating, for example, laryngotracheal injury. In some embodiments, the patch provides for wound healing and closure, minimizing the need for surgical suturing that can cause further tissue damage and inflammation. Tissue inflammation can be modulated via the inventive patch without the need for intralesional injections. Similar advantages can be expected to apply with respect to other mucosal surfaces of the body. This versatility will make the inventive patch a very valuable tool for medical professionals.

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1

Development of a Bioinspired, Self-Adhering and Drug-Eluting Laryngotracheal Patch Novel laryngotracheal wound coverage devices are limited by complex anatomy, smooth surfaces, and dynamic pressure changes and airflow during breathing. This example describes development and testing of a bioinspired mucoadhesive patch.

Polycaprolactone (PCL) fibers were electrospun onto a substrate and polyethylene glycol (PEG)—acrylate flocks in varying densities were deposited to create a composite patch. Sample topography was assessed with laser profilometry, material stiffness with biaxial mechanical testing, and mucoadhesive testing determined cohesive material failure on porcine tracheal tissue. Degradation rate was measured over 21 days in-vitro along with dexamethasone drug release profiles. Material handleability was evaluated via suture retention and in cadaveric larynges.

Increased flocking density was inversely related to cohesive failure in mucoadhesive testing, with a flocking density of PCL-PEG-2XFLK increasing failure strength to 6880±1810 Pa compared to 3028±791 in PCL-PEG-4XFLK density and 1182±262 in PCL-PEG-6XFLK density. The PCL-PEG-2XFLK specimens had a higher failure strength than PCL alone (1404±545 Pa) or PCL-PEG (2732±840). Flocking progressively reduced composite stiffness from 1347±15 to 763±21 N/m. Degradation increased from 12% at 7 days to 16% after 10 days and 20% after 21 days. Cumulative dexamethasone release at 0.4 mg/cm$^2$ concentration was maintained over 21 days. Optimized PCL-PEG-2XFLK density flocked patches were easy to maneuver endoscopically in laryngeal evaluation.

This novel, sutureless, patch is a mucoadhesive platform suitable to laryngeal and tracheal anatomy with drug delivery capability.

Materials and Methods:

Synthesis of Adhesive Patches. To fabricate dexamethasone-loaded polycaprolactone (PCL) electrospun fibers, PCL pellets (Mw: 80,000) were dissolved in chloroform and ethanol (15:85 v/v) and dexamethasone (1:10 Dexamethasone:PCL w/w) was added (Machado et al., Journal of the Brazilian Chemical Society, (2019), 30:1741-1750). Final solutions were electrospun at a traveling distance 30 cm, flow rate 1.4 ml/hr, and applied voltage of 25 KV.

Fiber mats created were soaked in 4-arm Polyethylene Glycol Acrylate (4APEGA, Mw:20,000, JenKem Technology, Plano, TX) dissolved in deionized water containing 0.1% 2-Hydroxy-4'-(2-hydroxyethoxy)-2-methylpropiophenone (Sigma-Aldrich, St. Louis, MO) in ethanol for 15 minutes to create an adhesive coating for flock attachment. Samples were then centrifuged (15 seconds at 500 rpm) to remove excess 4APEG. Coated fiber substrates were placed in the flocking system 5 cm from sieved 4APEGA stock, and various voltages (1, 2, 4, and 6 KV/cm) were applied to produce different flocking concentrations. The applied voltage forces flock particles to propel towards the fiber substrate (Walther et al., Materials, (2012), 5:540-557; Gossla et al., Acta biomaterialia, (2016), 44:267-276). Post-deposition, samples were exposed to UV light for 5 minutes to permanently bond flocks to the surface by crosslinking. Samples were re-immersed in dexamethasone (10 mg/ml), to load flocks with the drug. Table 1 lists the experimental groups. All chemicals were purchased from Thermofisher (Waltham, MA) unless otherwise specified.

TABLE 1

The description of designed groups and electro-flocking parameters.

| Group | Structure Description | Electro-flocking Electric Field |
|---|---|---|
| PCL | PCL electrospun fibers only | N/A |
| PCL-PEG | PCL electrospun fibers coated with 4APEGA | N/A |
| PCL-PEG-FLK | Flocked 4APEGA coated PCL fibers | 1 KV/cm |
| PCL-PEG-2XFLK | Flocked 4APEGA coated PCL fibers | 2 KV/cm |
| PCL-PEG-4XFLK | Flocked 4APEGA coated PCL fibers | 4 KV/cm |
| PCL-PEG-6XFLK | Flocked 4APEGA coated PCL fibers | 6 KV/cm |

Topographical Characterization. A Keyence VK-X200 laser microscope was used for three-dimensional profiling to quantify flock structure, height, and dispersion. Each specimen was mounted on a glass slide, a nine-quadrant grid was assigned around the specimen center (20× magnification), and upper and lower focus limits for the surface were set. Profilometry data was collected using VK Viewer software (v2.5, Keyence Corp., Osaka, Japan), imported into the multifile analyzer (v1.1.22.87, Keyence Corp.) and surface roughness, line roughness, and multiline roughness were computed for each sample (n=6/group).

Mechanical Property Characterization. Biaxial mechanical testing was conducted on biomaterial patches and on the inner layer of fresh porcine trachea using the BioTester (CellScale Biomaterials Testing, Ontario, Canada) (Davis et al., Urology, (2018), 113:235-240). 1.5 cm square specimens (n=10/group, n=30/trachea) were equilibrated in phosphate buffered saline (PBS) at room temperature. Specimen were held by rakes and stretched to 10% strain equibiaxially. The stress vs strain graphs for each direction were approximated by a sixth order polynomial using MATLAB_R2020A and the slope of the tangent line was calculated at 20% strain using the derivative of the polynomial to determine elastic modulus.

Swelling and Degradation Studies._1 cm square samples (n=6/group) were weighed before the experiment and placed in PBS buffer at 37° C. Swelling ratio was measured every 5 minutes by recording weight gain after removing excess PBS until swelling equilibrium (at 30 minutes). The degradation mass loss was recorded weekly over 21 days. The swelling or degradation ratio was calculated as $(M_f - M_i)/(M_i)$, where $M_i$ and $M_f$ are the mass of samples in its initial and final states, respectively.

Mucoadhesion Testing. Mucoadhesion was measured in single lap shear mode (using standard ASTM F2255) using a U-Stretch machine (CellScale Biomaterials Testing, Ontario, Canada). Samples (n=6/group) hydrated with PBS were cut 1 cm square strips and adhered to fresh porcine trachea. The adhesive joint was held compressed for two hours under 100 grams weight. Samples were then loaded to failure at 10 mm/min, and the cohesion strength measured.

Drug release behavior. Dexamethasone release from the drug-loaded PCL fibers, PCL-PEG, and samples with different flock concentrations was studied over 28 days (n=6/group) in PBS buffer at 37° C. To study burst release, the early release was measured after 15, 30, 60 and 120 minutes and to study sustained release, measurements were performed every 4 days over 28 days. Absorbance of dexamethasone at 290 nm[36] was measured using a plate reader and reported as mass/cm$^2$.

Suturability Testing. Suture retention strength was measured using the UStrech machine using an adapted AAMI protocol (Mine et al., Acta Medica Okayama, (2010), 64:121-128; Meng et al., RSC advances, (2019), 9:21258-21264; McKenna et al., Acta biomaterialia 2012; 8:225-233; Pensalfini et al., Journal of the Mechanical Behavior of Biomedical Materials, (2018), 77:711-717). Briefly, samples (n=6/group) were cut into 12×5 mm and polyglycolic acid 4/0 sutures were looped through each sample 2 mm from the free end. A ramp-to-failure test was executed at 10 mm/min until tear-out. The suture retention failure strength was normalized to sample thickness.

Cadaveric Material Testing. To determine patch handleability, realistic adhesion, and application in-vivo, fresh frozen cadaveric larynges were thawed to room temperature and placed in a hollow PVC pipe below a microscope to replicate microlaryngoscopy. Patches were trimmed to 1×2 cm for simulated use, hydrated in saline (n=6 technical replicates). Using a 400 mm microscope and microlaryngeal graspers, samples were passed into the larynx, overlaid on the vocal folds and then removed and pressed against the anterior wall of the subglottic and trachea. Material tears or pliability restrictions limiting maneuverability or positioning and the ability or lack of attachment to the mucosal lining were noted. All simulations were performed by a fellowship trained laryngologist.

Statistical Analyses. Numerical data are reported as average±standard error. Significant differences (at $p<0.05$) were identified using one-way Analysis of Variance (ANOVA), followed by Tukey's post hoc test, using SigmaPlot (v13, Systat Software Inc, San Jose, CA).

Results:

Scanning electron microscopy (SEM) demonstrated successful PCL electrospinning, uniform 4APEGA coating in the PCL-PEG group, and flock attachment to the substrate in PCL-PEG-FLK, PCL-PEG-2XFLK, PCL-PEG-4XFLK, and PCL-PEG-6XFLK groups. Less homogeneity of flocks were observed in PCL-PEG-FLK while flock concentration increased in PCL-PEG-2FLK and PCL-PEG-4XFLK groups where distinct flocks were visualized, and in the PCL-PEG-6XFLK group the flocks were increasingly aggregated (FIG. 1). The side profile view indicated an increase in flock height in groups with higher flock concentration. of large local clusters of 4APEGA flocks (FIG. 1).

Roughness measurements varied amongst the groups, visualized via Z heat maps and quantified by surface arithmetical (SA) mean height (FIG. 2). The Z heat maps (FIG. 2B), supported SEM observations, that flock height increased with flock concentration (deep blue and deep red represent the lowest valleys and highest peaks, respectively). It was observed that changes in SA (measured in μm); the difference between point heights compared to mean sample surface level did not correlate to applied voltage and consequently to flock concentration. While SA measurements were not significantly different, the highest SA values were recorded in the PCL-PEG-FLK (21±2.3 μm) and PCL-PEG-4XFLK (21.4±1.4 μm) groups while the lowest SA value was recorded for PCL (14.1±0.9 μm). The relatively lower SA of the PCL-PEG-6XFLK group (17.0±2.1 μm) quantitatively supports flock clusters forming on the substrate resulting in increased average surface height, but a decrease in calculated surface roughness.

Figure 3:
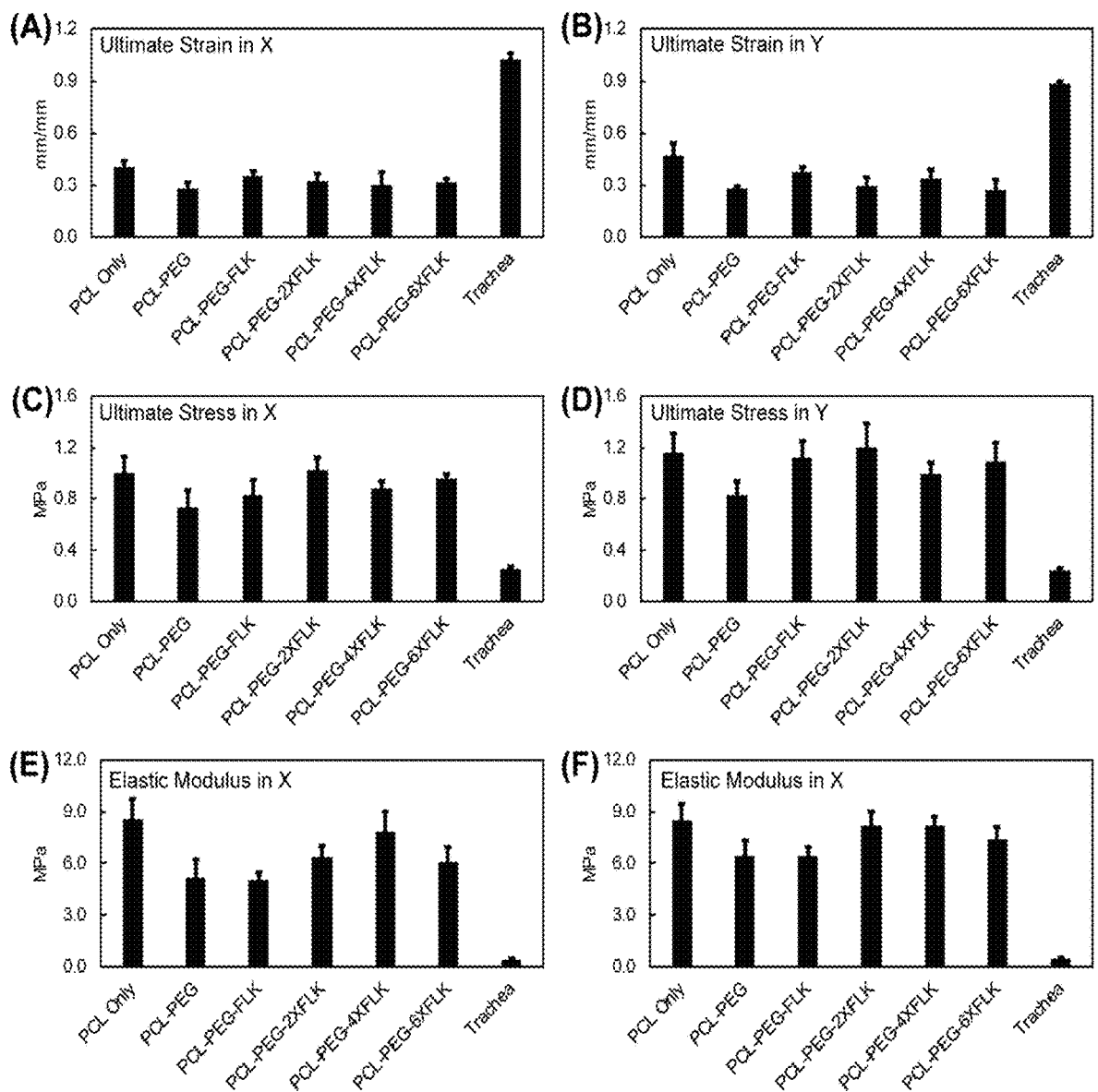
FIG. 3. Biaxial mechanical testing. The 6 different materials and native porcine tracheal tissue were tested in biaxial extension to failure and ultimate strain at failure in the (A) X and (B) Y direction, ultimate stress at failure in the (C) X and (D) Y direction and elastic modulus of the tissue in the (E) X and (F) Y direction were calculated. Tracheal properties were distinctly different from all other materials tested for all parameters ($p<0.001$), while there were no significant differences in material mechanics between the groups themselves, except that the PCL-PEG and PCL-PEG-FLK group had significantly lower elastic modulus than the PCL Only group ($p=0.05$).

Biaxial mechanical behavior measurements indicated minor numerical differences, but no difference in trends between groups for any metric between longitudinal and circumferential directions (FIG. 3). Elastic modulus ($p<0.0001$) and ultimate stress ($p=0.0001$) were significantly lower and ultimate strain was significantly higher ($p<0.0001$) in the native tracheal membrane, than all tested groups. Since the patches were designed to be homogenous, no differences were observed in mechanical properties along the two directions as anticipated. Further, no significant differences were measured in properties due to the coating or flocks.

Burst release over the first 2 hours and sustained dexamethasone release over 28 days was observed for all groups tested. A controlled burst release of dexamethasone was observed in the PCL-PEG-FLK, PCL-PEG-2XFLK, PCL-PEG-4XFLK, and PCL-PEG-6XFLK groups (FIG. 4A) over the first 2 hours which is associated with the presence of 4APEGA either in the coating or the flocks and the burst release correlated with flock concentration. Over 28 days (FIG. 4B), the remaining drug was associated with dexamethasone incorporated in PCL fibers and a sustained release was observed across all groups. The PCL fiber mat demonstrated the lowest drug release (~4 mg/cm$^2$), while the 4APEGA coated and flocked patches released~14 mg/cm$^2$ of dexamethasone over 28 days.

Swelling ratio is crucial to drug release behavior since diffusion of water into the 4APEGA network leads to dexamethasone dissolution. Additionally, mucoadhesion forces must overcome the swollen weight of the adhesive patch to ensure it remains in place, making it a crucial design consideration. The groups tested reached swelling equilibrium after 15 minutes, further explaining diffusion-based burst release behavior (FIG. 5A). The highest degradation was observed in the PCL-PEG (48.8±3.1%), PCL-PEG-FLK (52.4±1.5%), and PCL-PEG-2XFLK (53.4±3.5%) groups while degradation was significantly lower in PCL only (17.8±1.8%) and PCL-PEG-6XFLK (9.8±1.8%) groups (FIG. 5B). Specifically, the degradation in PCL and PCL-PEG-6XFLK groups was significantly lower than in PCL-PEG-FLK and PCL-PEG-2XFLK groups for all time points day 7 and later, and lower compared to PCL-PEG at day 14 and later ($p<0.03$). 4APEGA is known to have low degradation rate due to high molecular weight[41]; and therefore, agglomeration of flocks resulted in a more stable structure resistant to flock detachment while in other groups with more dispersed flocks, detachment resulted in higher mass loss (FIG. 5B).

The highest mucoadhesive strength was observed in the PCL-PEG-2XFLK group (6879 Pa), and the lowest adhesion was observed for PCL-PEG (1053 Pa) (FIG. 6). PCL-PEG-2XFLK patches showed significantly higher adhesion to mucosa compared to PCL alone, PCL-PEG, PCL-PEG-FLK, and PCL-PEG-6XFLK ($p=0.004$, 0.042, 0.002, and 0.004, respectively) but not PCL-PEG-4XFLK flocking ($p=0.092$).

Sample testing in simulated microlaryngoscopy cases revealed pliable, easily handled and manipulated patches (FIG. 7A). Patches were found to adhere to the subglottic/trachea mucosa but also allowed for adjustment/manipulation for position optimization. FIG. 7B illustrates tear-out failure resistance in suture retention of the engineered patches. The lowest suture retention strength was recorded in PCL (0.45±0.13N) and an increasing trend was observed with increasing flock concentration, the highest suture retention strength was measured for PCL-PEG-6XFLK (3.5±0.7N) (FIG. 7C). Suture retention strength in PCL- PEG-6XFLK was significantly higher than in PCL PCL-PEG, and PCL-PEG-FLK groups (p=0.001, p=0.022 and p=0.023 respectively).

Discussion:

Translational implementation of novel materials and therapeutic delivery systems is needed for the management of laryngotracheal and esophageal wounds. Medical adjuncts such as steroids, antibiotics, and anti-inflammatory medications have been studied clinically, but an urgent need for efficient delivery approaches remains (Davis et al., Translational Cancer Research, (2020), 9:2108-2116; Tan et al., Acta Biomaterialia, (2020). Intralesional and in-office steroid injection remain current best practice for subglottic and tracheal stenosis (Wierzbicka et al., J Laryngol Otol, (2016), 130:674-679; Hoffman et al., Laryngoscope, (2017), 127:2475-2481; Franco et al., Laryngoscope, (2018), 128:610-617). These interventions appear to reduce disease progression and increase interval between repeat procedures. Despite compelling evidence for their effectiveness, application of corticosteroids to the stenotic region remains limited by practical considerations of performing in-office injection involving flexible videolaryngoscopy and transcutaneous injection (Franco et al., Laryngoscope, (2018), 128:610-617). Leveraging our novel patch allows for continuous drug delivery across the desired surface, filling an unmet clinical need. In addition to expanding the possible dose and durations for steroid treatment, this approach could reduce currently necessary injections. Similarly, few effective adjuvant therapies are available for glottic webs beyond keels and stents (Fussey et al., J Laryngol Otol, (2019), 1-8). Interest in improved management of webs is evidenced by recent studys exploring bovine pericardium as a potential graft material and advanced surgical closure techniques (Zapater et al., Laryngoscope, (2019), 129:2121-2124; Yilmaz et al., Laryngoscope, (2019), 129:1423-1427). Our novel patch could fill this role and be used with or without accompanying drug delivery.

Topography and surface contact area play a large role in final adhesive forces (Kim et al., Applied Physics Letters, (2007), 91:221913). Hydrogel based adhesives demonstrate enhancement via interlocking mechanisms activated by swelling of PEG components (Mandavi et al., Proceedings of the National Academy of Sciences, (2008), 105:2307-2312). Surface roughness is critical to mucoadhesive properties and mucosa-material interaction is multifactorial, with contributions from moisture, surface roughness, and surface area/shape (Tamelier et al., *SENSORS, 2011 IEEE*, 2011: 1819-1822.; Mandavi et al., Proceedings of the National Academy of Sciences, (2008), 105:2307-2312). The gecko's ability to adhere to surfaces using setae on its feet, involves factors including water contact angle, Van der Waals forces, capillary forces, and geometry (Autumn et al., *Biological Adhesives*. Berlin, Heidelberg: Springer Berlin Heidelberg, 2006:225-256). In our study, both roughness and surface contact area varied with flock density (FIGS. 1, 2). Differences in roughness and inherent to varying patch designs in our study allowed for optimal design selection in terms of surface flock density. A very low density of flocks on the patch resulted in low adhesive force to tracheal mucosa which first increased and then decreased at higher surface flocking densities (FIG. 6). Furthermore, preload plays a crucial role in the ultimate adhesive properties. In our evaluation, all samples had equivalent preload force and duration prior to quantification. The improved cohesive adhesion of PCL-PEG-2XFLK in our study can be attributed to an optimized flock concentration leading to mechanical interlocking between the flocks and mucin layer of the tracheal wall. Conversely, the PCL-PEG-4XFLK and PCL-PEG-6XFLK groups have higher flock concentrations, and the lower adhesion properties in these groups could be related to decreased available area for adhered surface-flock interaction.

The adhesive properties of the patch are particularly critical in the moist environment of the trachea and esophagus. Sufficient mucoadhesion is also necessary for efficient and optimized drug delivery (S. Pendekal et al., Acta Pharmaceutica Sinica B, (2012), 2:318-324; Shaikh et al., J Pharm Bioallied Sci 2011; 3:89-100. To date, an effective route of predictable corticosteroid delivery to local tissue remains elusive. In the nasal cavity, dexamethasone stents showed promise in modulating wound healing (Beule et al., Laryngoscope, (2008), 118:2073-2077). Our novel flocked patch effectively delivered a sustained release of corticosteroid over 28 days while also providing an initial burst release. The initial burst observed during the first 2 hours was related to the higher PEG volume of flocks. Also, the presence of flocks caused greater drug release compared to PCL-PEG, underlining the impact of flocks on the uptake and release of dexamethasone. Jointly, the adhesive properties prevent unintentional dislodgement, but post-release flock degradation permits removal for follow-up evaluations or at the conclusion of planned treatment.

While different implant-based drug delivery approaches have been developed for otorhinolaryngology applications, less attention has been paid to handleability, suturability, and general mechanical suitability (Tan et al., Acta Biomaterialia, (2020). Mechanical forces play a prominent role in fibrosis through T-cell mediated prolonged inflammation (Boazak et al., ACS Biomaterials Science & Engineering, (2018), 4:1272-1284). Modified interfaces with highly adhesive surfaces and reinforced mechanical properties provide a customizable therapeutic platform which can benefit laryngotracheal wound treatments. While mechanical properties of the patches are comparable to native tissue, the specific impact of differential mechanical stiffness on fibroblast recruitment and epithelialization requires further study.

Critically, the study was limited to in vitro, ex vivo, and cadaveric testing. The degradation and drug delivery tests were conducted over 28 days, because practically, most non-bioresorbable patches, stents, keels and glottic webs are typically removed 10-14 days after placement. Materials used in our patch match those currently used without cytotoxicity in other FDA approved devices, and can be further assessed in future preclinical in vivo tests. Mucoadhesion testing was performed on excised porcine trachea with reproducible preload force. However, the tracheal microenvironment in vivo varies from the ex vivo counterpart with increased local temperature, mucocilliary function, and a distinct local microbiome which may confer additional adhesion based on flocking; though in vivo studies are needed to quantify differences. The capacity of the flocked patch to remain secure to the laryngotracheal complex without unintentional sloughing can also better be assessed in future in vivo studies. Similarly, outside of intranasal dexamethasone stent evaluation, optimal concentration for continuous steroidal delivery to laryngotracheal wounds remains unknown. Despite these limitations, the in vitro, ex vivo and cadaveric testing of the self-adhering patch permitted design optimization and preparation for preclinical testing towards clinical application.

This novel, sutureless, patch is a mucoadhesive platform suitable to laryngotracheal anatomy with drug delivery capability. Testing supports the translational potential of this technology for further preclinical evaluation.

What is claimed is:

1. A mucoadhesive patch for attachment to a mucosal surface in a patient, the patch comprising a fibrous polymeric mat substrate and a plurality of polymeric flock particles that are attached to the substrate, the patch being reversibly attachable to the mucosal surface, wherein the fibers of the polymeric mat substrate comprising at least one of polycaprolactone (PCL), poly(lactic-co-glycolic acid (PLGA) and polymethylmethacrylate (PMMA), the flock particles comprising polyethylene glycol diacrylate (PEGDA).

2. The mucoadhesive patch of claim 1, wherein the fibers of the polymeric mat substrate comprise PCL.

3. The mucoadhesive patch of claim 2, the patch incorporating a drug to be delivered to a region of the mucosal surface.

4. The mucoadhesive patch of claim 3, wherein the patch exhibits sustained release of the drug over a period of at least 28 days.

5. The mucoadhesive patch of claim 3, wherein the drug is an anti-inflammatory drug.

6. The mucoadhesive patch of claim 1, wherein fibers of the fibrous polymeric mat substrate are formed from a monomer solution by electrospinning, wherein a drug to be delivered to a region of the mucosal surface can be included in the monomer solution prior to the electrospinning.

7. The mucoadhesive patch of claim 6, wherein the flock particles were drawn to the substrate using an applied potential.

8. The mucoadhesive patch of claim 7, wherein a magnitude of the applied potential determines a concentration of the flock particles on the substrate.

9. The mucoadhesive patch of claim 1, wherein the flock particles are attached to the substrate by covalent crosslinking.

10. The mucoadhesive patch of claim 1, the patch being capable of closing an esophageal or laryngotracheal wound in a patient.

* * * * *